US010932962B2

(12) United States Patent
Drewnowski et al.

(10) Patent No.: US 10,932,962 B2
(45) Date of Patent: Mar. 2, 2021

(54) RECLOSABLE WRAPPER FOR SANITARY PRODUCTS AND RELATED METHODS

(71) Applicant: Edgewell Personal Care Brands, LLC, Chesterfield, MO (US)

(72) Inventors: Wojtek Drewnowski, Richmond, VA (US); Pankaj Nigam, Ridgewood, NJ (US); Adebimpe Ogunade, Saddle Brook, NJ (US); Yukiko Naoi, New York, NY (US); Jeffrey Kapec, Westport, CT (US)

(73) Assignee: EDGEWELL PERSONAL CARE BRANDS, LLC, Chesterfield, MO (US)

( * ) Notice: Subject to any disclaimer, the term of this patent is extended or adjusted under 35 U.S.C. 154(b) by 255 days.

(21) Appl. No.: 14/210,724

(22) Filed: Mar. 14, 2014

(65) Prior Publication Data
US 2014/0276351 A1 Sep. 18, 2014

Related U.S. Application Data

(60) Provisional application No. 61/789,539, filed on Mar. 15, 2013.

(51) Int. Cl.
*A61F 13/551* (2006.01)
*B65B 67/08* (2006.01)
(Continued)

(52) U.S. Cl.
CPC ........ *A61F 13/55185* (2013.01); *B65B 11/50* (2013.01); *B65B 11/56* (2013.01);
(Continued)

(58) Field of Classification Search
CPC ............ A61F 13/55175; A61F 13/5518; A61F 13/55185; A61F 2013/55195
See application file for complete search history.

(56) References Cited

U.S. PATENT DOCUMENTS

| 4,648,513 A | 3/1987 | Newman | |
|---|---|---|---|
| 4,726,805 A * | 2/1988 | Sanders, III | .......... A61F 13/263 604/15 |

(Continued)

FOREIGN PATENT DOCUMENTS

| WO | 200119309 A1 | 3/2001 |
|---|---|---|
| WO | 200251718 A1 | 7/2002 |

(Continued)

*Primary Examiner* — Bradley H Philips

(57) ABSTRACT

A wrapped sanitary product comprises a wrapper and a sanitary product that provides for discreet storage and removal of a sanitary product, and/or discreet placement of a soiled sanitary product into a vacated wrapper to be discreetly disposed thereafter. The wrapper is formed such that an interior space is created to store a sanitary product. The wrapper has a storage configuration, and accessible configuration, and a second storage configuration. The wrapper has a port that provides access to the interior space and the sanitary product therein. The wrapper has a flap that can comprise a sticker or a tab, or both. The flap is sealed to the wrapper in a storage configuration, is at least partially removable from the wrapper in an accessible configuration, and is reclosable to the wrapper in a second storage configuration.

15 Claims, 13 Drawing Sheets

(51) Int. Cl.
    *B65B 11/50*   (2006.01)
    *B65B 11/56*   (2006.01)
    *B65B 25/00*   (2006.01)
    *B65D 75/58*   (2006.01)

(52) U.S. Cl.
    CPC .............. *B65B 25/00* (2013.01); *B65B 67/08* (2013.01); *B65D 75/5833* (2013.01); *B65D 2575/586* (2013.01)

(56) References Cited

U.S. PATENT DOCUMENTS

| | | | |
|---|---|---|---|
| 4,881,644 A * | 11/1989 | Norquest | A61F 13/55185 206/363 |
| 5,133,457 A | 7/1992 | Kadel | |
| H1363 H | 10/1994 | Leeker | |
| 6,203,512 B1 | 3/2001 | Farris et al. | |
| 6,497,692 B1 | 12/2002 | Tameishi et al. | |
| 7,073,666 B2 | 7/2006 | Arndt | |
| 7,101,358 B2 | 9/2006 | Domeier et al. | |
| 7,442,105 B2 | 9/2008 | Loyd | |
| 7,596,929 B2 | 10/2009 | Arndt | |
| D619,478 S | 7/2010 | Drewnowski et al. | |
| 7,972,318 B2 | 7/2011 | Nijs et al. | |
| 8,282,280 B2 | 10/2012 | Germanow et al. | |
| 8,302,844 B2 | 11/2012 | McConnell et al. | |
| 8,317,765 B2 | 11/2012 | Loyd et al. | |
| 8,986,272 B2 | 3/2015 | Loyd et al. | |
| 2003/0065300 A1 * | 4/2003 | Suga | A61F 13/55185 604/385.02 |
| 2004/0112779 A1 | 6/2004 | Arndt | |
| 2004/0232024 A1 | 11/2004 | Guerreschi et al. | |
| 2005/0098466 A1 | 5/2005 | Thomas | |
| 2007/0151885 A1 | 7/2007 | Loyd et al. | |
| 2007/0244454 A1 | 10/2007 | Fujikawa et al. | |
| 2009/0247981 A1 | 10/2009 | Glaug et al. | |
| 2010/0076393 A1 | 3/2010 | Wasson et al. | |
| 2010/0094238 A1 | 4/2010 | Scarano | |
| 2010/0243500 A1 | 9/2010 | McConnell et al. | |
| 2011/0132976 A1 | 6/2011 | Drewnowski et al. | |
| 2011/0184367 A1 * | 7/2011 | Toms | A61F 13/551 604/385.02 |
| 2011/0203229 A1 * | 8/2011 | Exner | B31B 1/25 53/462 |
| 2011/0229059 A1 | 9/2011 | Hanna et al. | |
| 2012/0330265 A1 | 12/2012 | Germanow et al. | |
| 2015/0141945 A1 | 5/2015 | Emergi | |
| 2015/0257949 A1 | 9/2015 | Thompson et al. | |

FOREIGN PATENT DOCUMENTS

| | | |
|---|---|---|
| WO | 2008019132 A1 | 2/2008 |
| WO | 2009120732 A1 | 10/2009 |

* cited by examiner

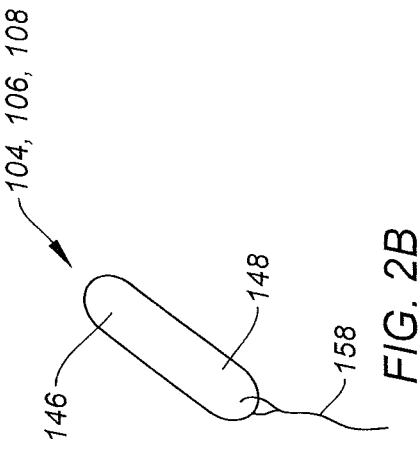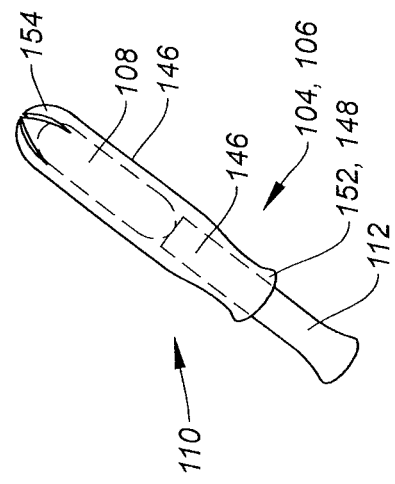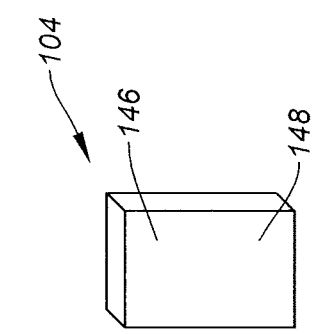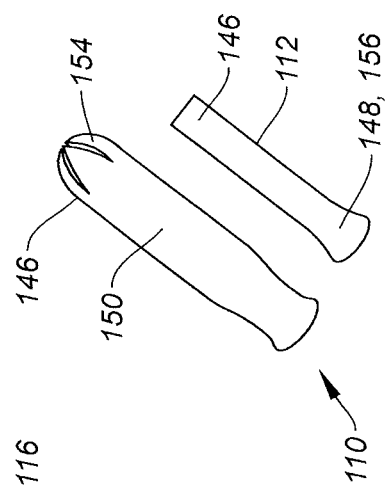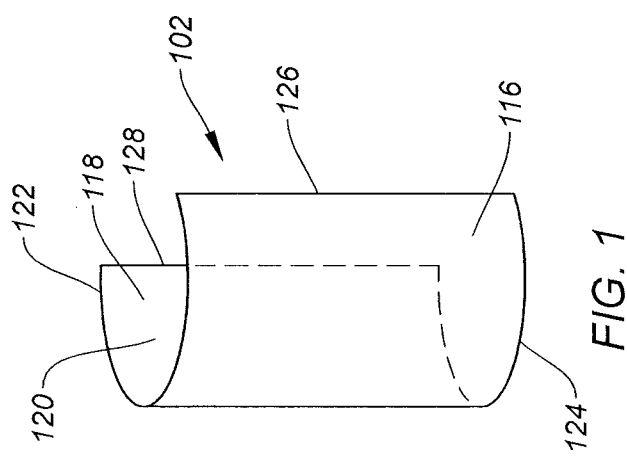

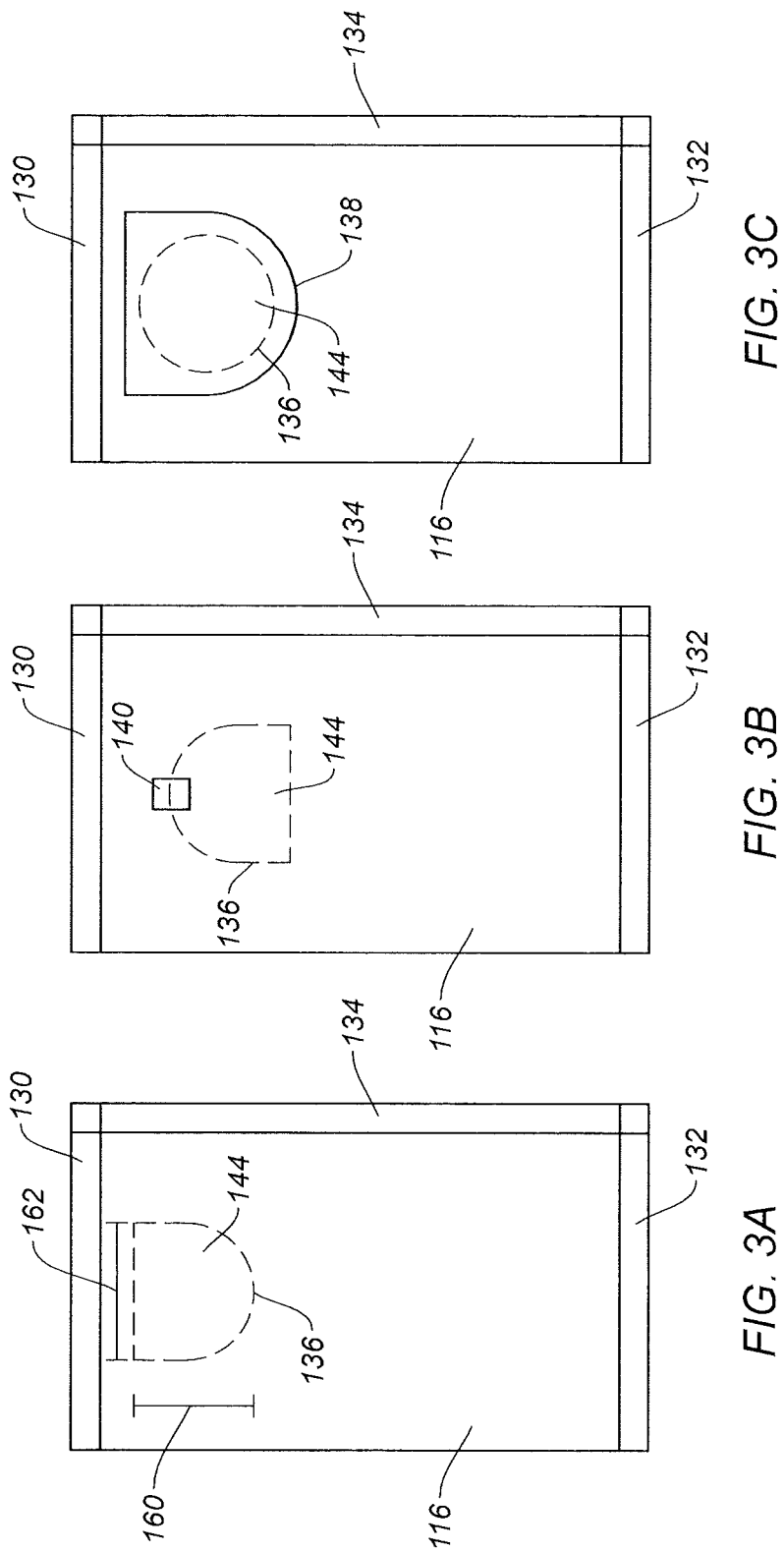

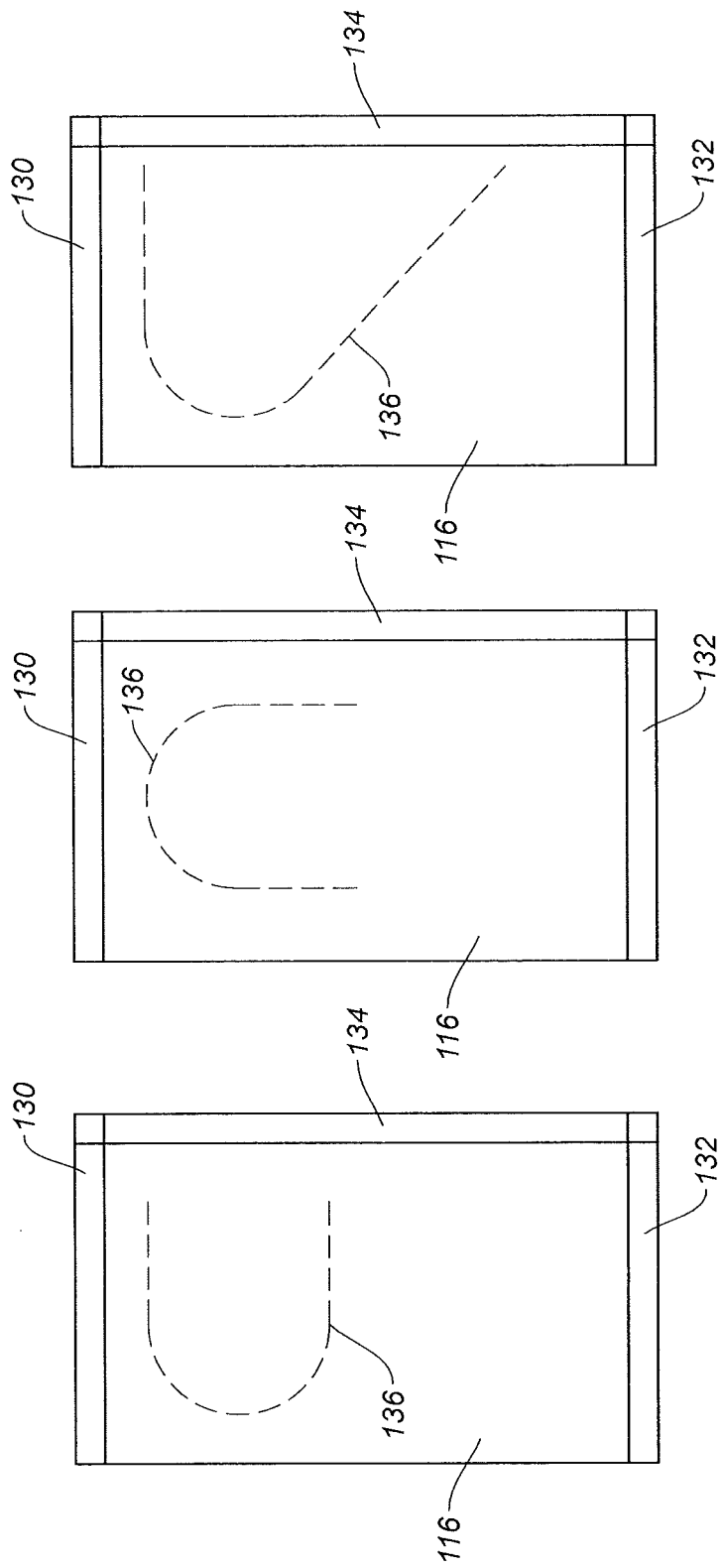

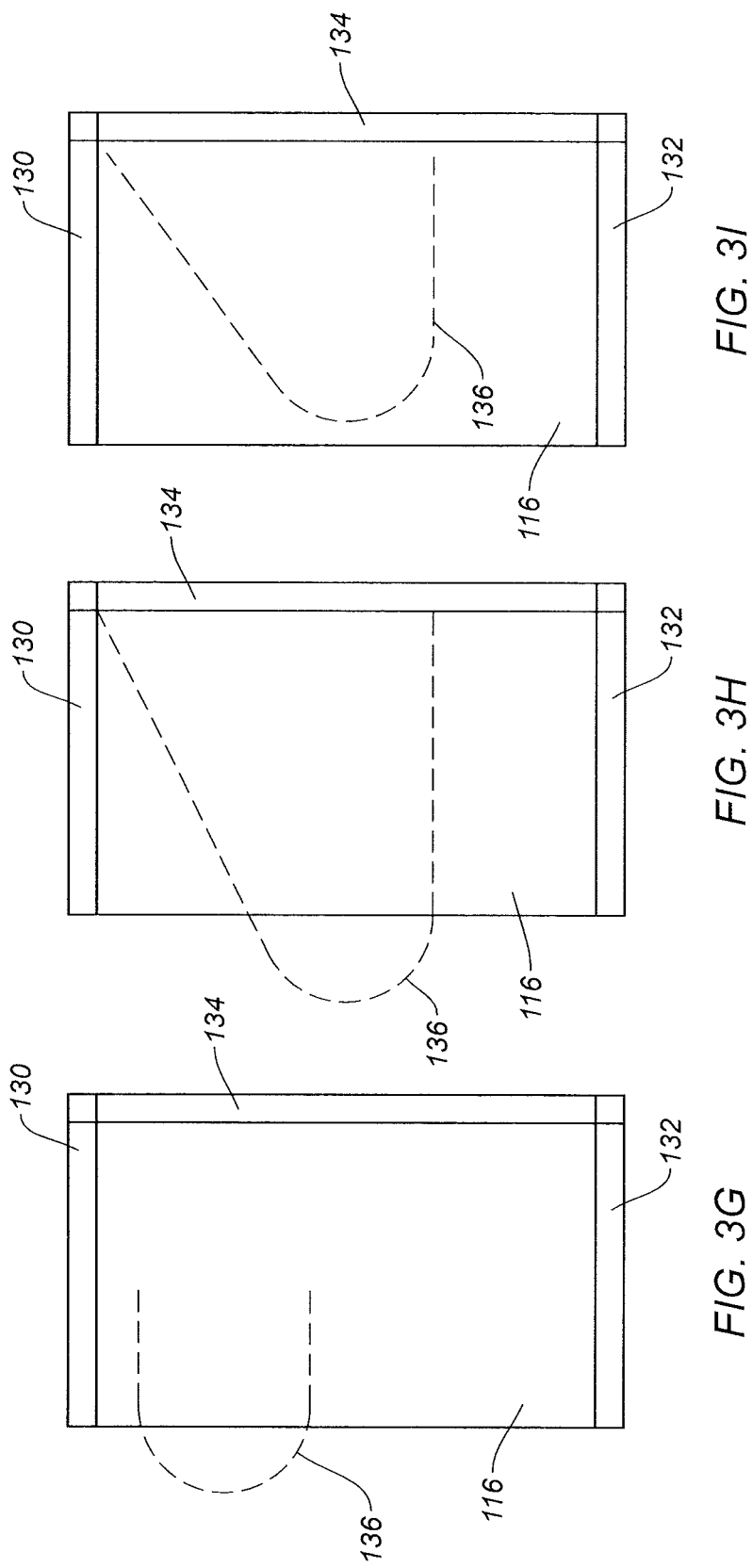

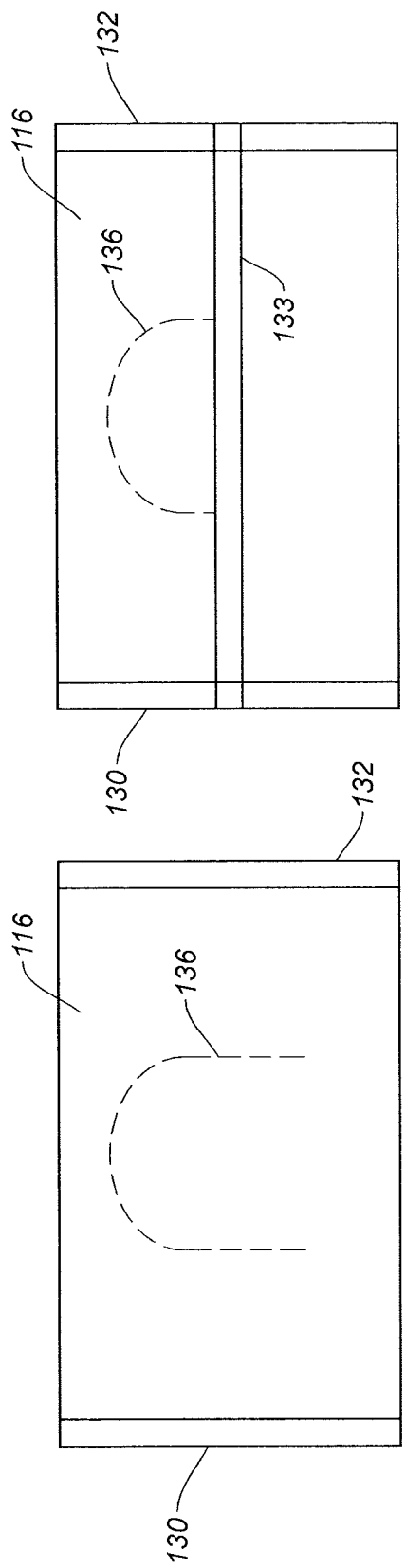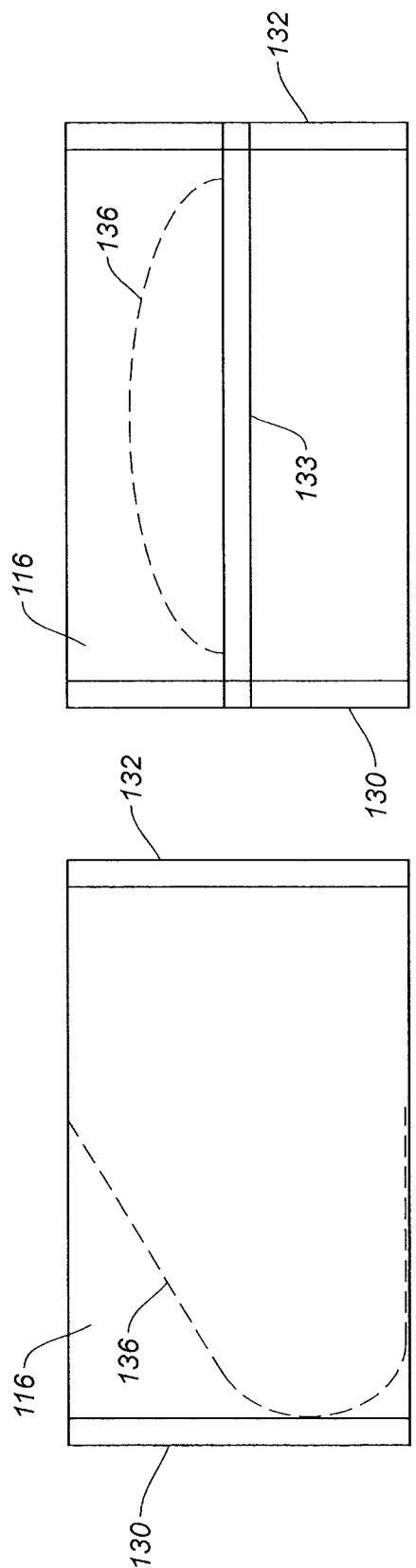

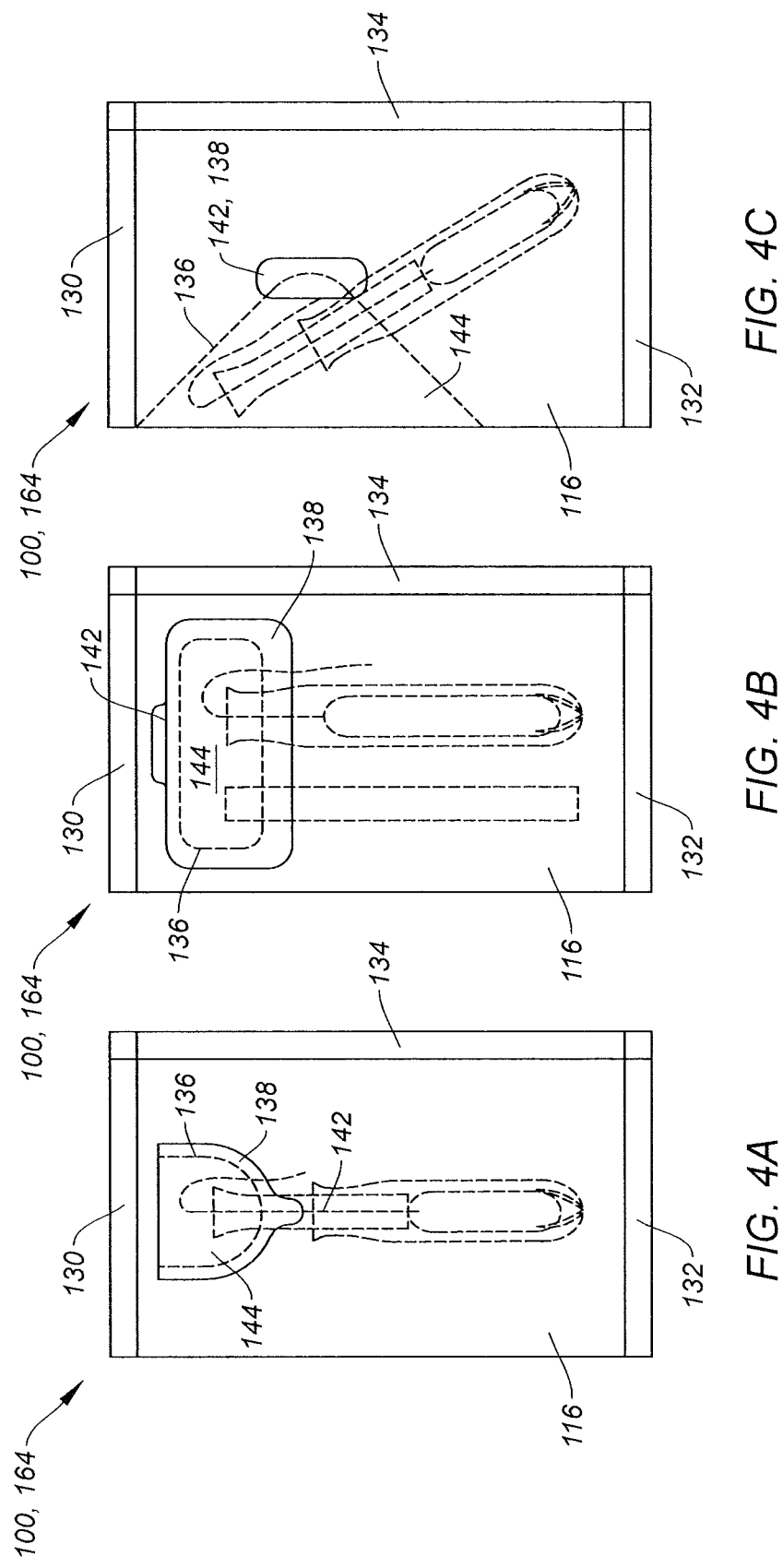

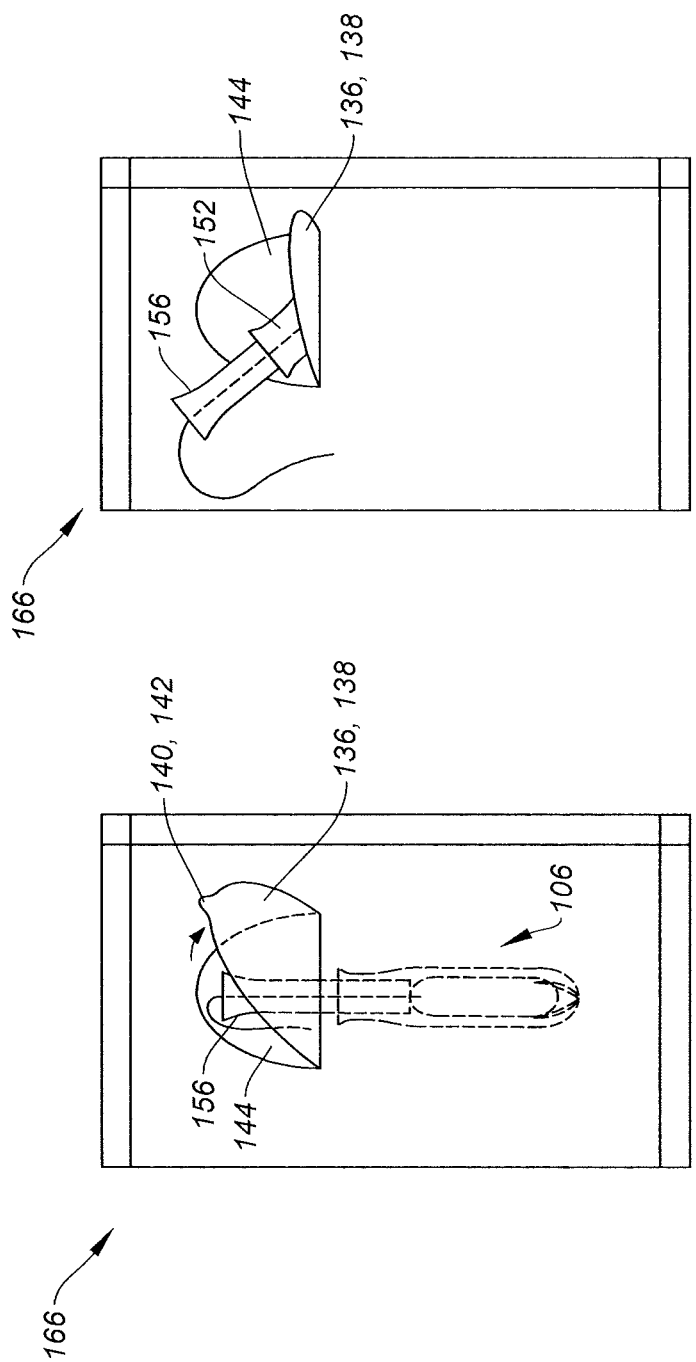

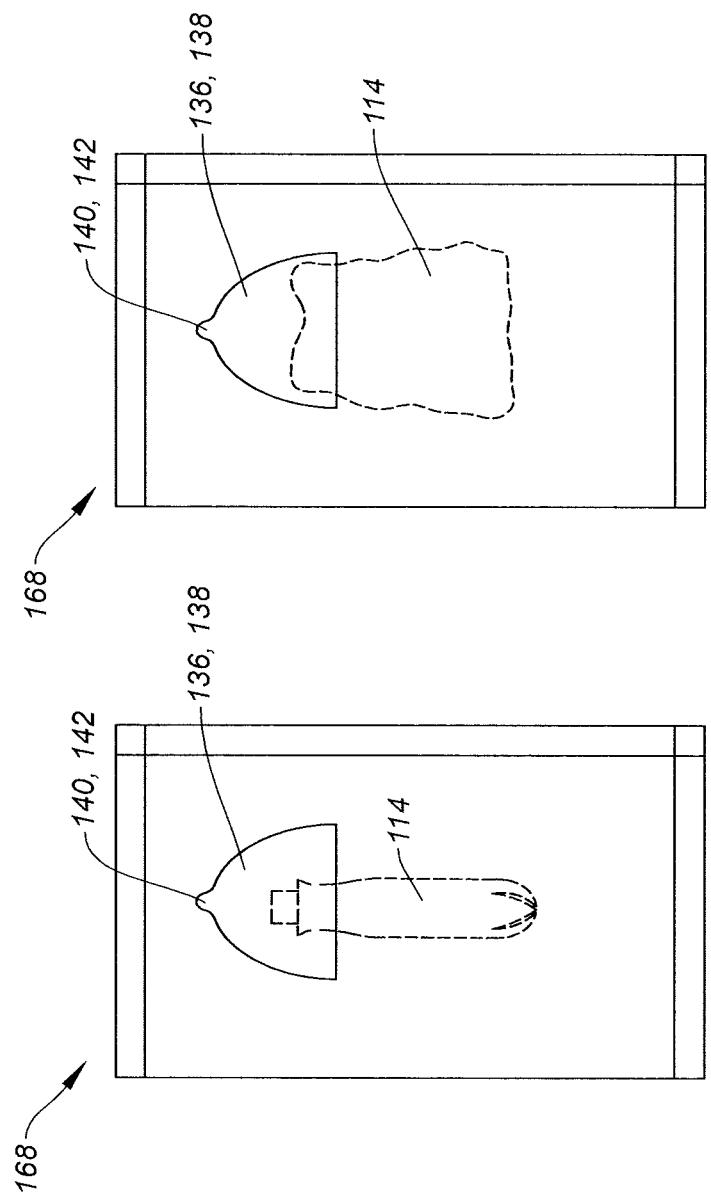

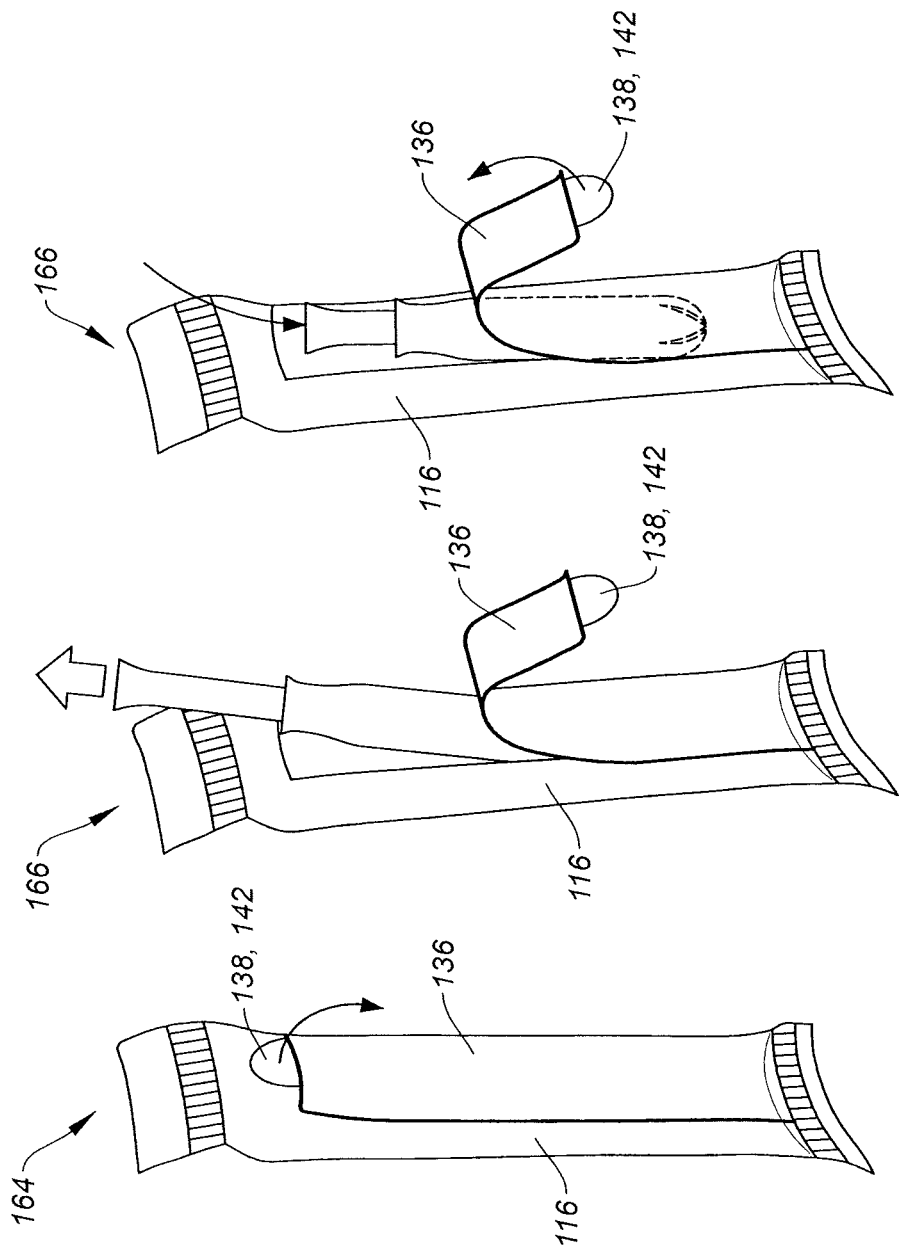

RECLOSABLE WRAPPER FOR SANITARY PRODUCTS AND RELATED METHODS

BACKGROUND OF THE INVENTION

A. Field of Endeavor

The present disclosure is related to wrappers for sanitary products such as but not limited to feminine care products. More particularly, the present disclosure is related to wrappers that facilitate storage/maintenance of sanitary products, easy removal of a sanitary product from the wrapper, inserting a soiled sanitary product back into the vacated wrapper, and sealing the soiled sanitary product within the wrapper for discreet disposal.

B. Background Information

Sanitary products such as but not limited to tampons, pads, liners, incontinence devices, labial pads, sanitary napkins and pessaries are commercially produced and sold to consumers with wrappers. Wrappers provide protection of the sanitary product (i.e., tampon) from being soiled prior to use. In the example of tampons, the wrapper is opened, the tampon is removed from the wrapper and inserted into the body. If the tampon has an applicator, the applicator will contact fluids from the user's body during insertion. The user must undesirably handle the used applicator prior to disposal after insertion. The wrapper and applicator are generally discarded.

In the example of other sanitary products such as napkins, pads, liners, digital tampons, etc., a soiled sanitary product must also be undesirably handled prior to disposal and/or replacement with a new sanitary product.

Sanitary product wrappers made of polyolefin films based material such as, for example, polypropylene or polyethylene, currently available to consumers produce noise or sound upon a user tearing the wrapper to access the tampon. The noise can be heard by others, and thus does not allow the user to be discreet while using a sanitary product. However, material other than polypropylene can be undesirably difficult to open.

Some prior art wrappers have a perforated line to assist the user to open the wrapper. Many prior art wrappers merely print an indicator on the wrapper to indicate where this perforated line is to the user. Other prior art wrappers include one or more die cuts at the sealed end leading into the perforated line. Unfortunately, these die cut ends result in "chads" needing to be removed from the wrapper and generate excess waste, further processing steps, and induce the risk of clogging machinery if not properly removed.

In order to manufacture many of the aforementioned wrappers, complex or sophisticated tooling can be required to accommodate wrappers with external flaps or tabs. It would be beneficial and advantageous from a manufacturing standpoint to utilize simpler and/or existing machinery and add a secondary item or step to a manufacturing process in order to provide a more suitable wrapper for sanitary products as opposed to completely retooling or buying new or more sophisticated tooling in order to achieve a similarly purposed wrapper.

Accordingly, there is a need for wrappers for sanitary products and methods related thereto that overcome, alleviate, and/or mitigate one or more of the aforementioned deficiencies of prior art wrappers.

SUMMARY

The present disclosure provides a wrapper for a sanitary product having an exterior face and an interior face. The wrapper has a first end disposed opposite to a second end and a first side disposed opposite to a second side. An interior space is defined by the interior face upon the joining of the first side to the second side, the first end being joined to itself and the second end being joined to itself. Alternatively, the interior space can be defined by the interior faces of two or more sheets being joined at free ends.

A sanitary product has an insertion end and a withdrawal end. In some embodiments, a sanitary product is a tampon. In some embodiments of a tampon, the tampon can comprise a tampon pledget. In another embodiment of a tampon, the tampon can comprise a tampon pledget and a tampon applicator. The tampon pledget has an insertion end and a withdrawal end. Optionally, the tampon pledget can have a withdrawal string. The tampon applicator has a barrel region and a fingergrip region, where the fingergrip region is a withdrawal end. A tampon pledget is housed within the barrel region. The barrel region has an insertion end typically comprising flexible petals. The barrel region and fingergrip region can be integral or multiple separate pieces that are fastened together by mechanical, chemical, adhesive or other means. The tampon can also comprise a plunger with an insertion end and a gripping end. The plunger can telescopically engage the tampon applicator such that the plunger is capable of being at least partially internal to the tampon applicator. The plunger can be initially separate from the tampon applicator, or, in other embodiments, the plunger can be integral with or mechanically attached to the tampon applicator. In an initial state, the plunger can be at least partially telescopically engaging the tampon applicator, or the plunger can be external to the tampon applicator in a side-by-side or other configuration.

The wrapper has a port that allows access to the interior space. The port can also be created from the wrapper material through the act of opening the flap. A part of the wrapper can preferentially stay attached to the flap in the act of creating the port. As hereinafter defined, the term "port" describes an opening, communication, passageway, pathway, hole or other similar adjectives that allows a secluded space to be accessed from outside that secluded space. The secluded space is at least a portion of the interior space, or the entire interior space. The port can be oriented in a number of places along the exterior face of the wrapper, the port can be any number of geometric shapes and sizes in order to provide enough space for a user to grasp a sanitary product within the interior space and remove the sanitary product from the wrapper. Preferably, the port is sized, shaped and positioned such that the withdrawal end, gripping end, fingergrip region and/or the plunger can be discreetly and easily obtained by a user's fingers and removed from the wrapper. Further, the port is sized, shaped and positioned such that a user can insert a soiled sanitary product back into the wrapper for discreet disposal.

The wrapper has a flap that seals the wrapper in a storage configuration. The flap is positioned over the port and seals to the exterior face. The flap can be integrally formed with the wrapper and can be at least partially cut, have perforations, slits, score lines, cuts or other lines of weakness such that the user can grasp the flap and discreetly remove it to reveal the interior space and the sanitary product contained therein. In other embodiments, the flap can be a separate component or material such as a material with a resealable and/or adhesive backing. In other embodiments, the flap can have a portion that is integral with the wrapper and a portion that is a separate component or material. In another embodiment, the flap can be such that it extends beyond the longitudinal seal or the end seal or both. In one embodiment, the flap is integral with the wrapper and is die cut such that the flap is sized similar to the port. In another embodiment, the flap is integral with the wrapper and at least partially covers the port. The flap can further comprise a sticker that is affixed at least partially to the exterior face of the wrapper. The sticker at least partially covers the port and/or at least partially covers the flap. In embodiments with the sticker, the flap and the sticker, in combination, completely cover the port. The flap, sticker, or both can be congruently shaped to the port or can differ in shape, for example, the flap and sticker, in combination, can be larger than the port such that the port is completely covered before the wrapper is opened. The sticker can extend beyond the longitudinal seal or the end seal or both. The sticker is sealable to the exterior face such that the wrapper has a stored configuration that maintains the hygienic environment of the sanitary product within the interior space of the wrapper. As used herein, the term "stored configuration", "stored" or "storing", include storage configurations wherein said sanitary product and/or wrapped sanitary product are in transit in a box or carton, in a hand bag, purse, duffel bag, or other personal item carrying device, or otherwise stored in a lavatory, bathroom, in a cabinet, on a shelf, or any other storage area/position or transportation configuration. The sticker can be removed from the exterior face of the wrapper such that it also draws the flap away and reveals the port in an accessible configuration. In the accessible configuration, the user is able to remove the sanitary product from the interior space. Once vacated, the user is able to insert a soiled sanitary product into the interior space and reseal the flap in order to contain the soiled sanitary product for discreet disposal.

The flap, sticker or both can have a tabbed portion that allows the user to easily grasp the flap and remove the flap away from the port or to replace the flap over the port.

In embodiments where the flap is integral with the wrapper, the flap may be scored about the integral portion where the flap and wrapper meet and form a boundary of the port. This scored integral portion assists in the wrapper, once opened, to remain in an open position. This is advantageous in that the score creates an enhanced hinge about which the flap can bend and remain in an open position. In embodiments comprising a sticker, the sticker may be located such that an end coincides with the scored portion of the flap or is located such that the sticker does not overlap the integral portion of the flap and wrapper, and thereby enables the flap to remain in an open position. In embodiments also having a tab, the same principles previously discussed for the flap and sticker also apply.

In other embodiments, the flap, sticker, tab, or combinations thereof, may be oriented such that the center of mass is positioned beyond the midsection of the flap, sticker, tab, or combinations thereof. In these embodiments, the center of mass is located towards the portion of the flap, sticker, tab, or combinations thereof that is initially grasped by the user such that the wrapper, once opened, will remain in an open position. The center of mass in its location between the midsection of the flap, sticker, tab, or combinations thereof, and the opening end of the flap, sticker, tab, or combinations thereof, biases the flap, sticker, tab, or combinations thereof to remain in an open configuration.

In other embodiments, the flap, sticker, tab, or combinations thereof, are of a material that is sufficiently rigid or stiff such that a user is able to flick the wrapper from an open position to a resealed condition. This is advantageous in that it requires less manipulation in order to reseal the wrapper and discreetly dispose of the soiled sanitary product.

BRIEF DESCRIPTION OF THE SEVERAL VIEWS OF THE DRAWINGS

FIG. 1 is a representation of an embodiment of film for a wrapper

FIG. 2A is a representation of an embodiment of a sanitary product

FIG. 2B is a representation of an embodiment of a tampon

FIG. 2C is a representation of an embodiment of a tampon applicator

FIG. 2D is a representation of an embodiment of a tampon

FIG. 3A is a representation of an embodiment of a wrapper

FIG. 3B is a representation of an embodiment of a wrapper

FIG. 3C is a representation of an embodiment of a wrapper

FIG. 3D is a representation of an embodiment of a wrapper

FIG. 3E is a representation of an embodiment of a wrapper

FIG. 3F is a representation of an embodiment of a wrapper

FIG. 3G is a representation of an embodiment of a wrapper

FIG. 3H is a representation of an embodiment of a wrapper

FIG. 3I is a representation of an embodiment of a wrapper

FIG. 3J is a representation of an embodiment of a wrapper

FIG. 3K is a representation of an embodiment of a wrapper

FIG. 3L is a representation of an embodiment of a wrapper

FIG. 3M is a representation of an embodiment of a wrapper

FIG. 4A is a representation of an embodiment of a wrapped sanitary product such as a tampon FIG. 4B is a representation of an embodiment of a wrapped sanitary product such as a tampon FIG. 4C is a representation of an embodiment of a wrapper sanitary product such as a tampon FIG. 7A is a representation of an embodiment of a wrapped sanitary product such as a tampon in an accessible configuration FIG. 7B is a representation of an embodiment of a wrapped sanitary product such as a tampon in an accessible configuration FIG. 7C is a representation of an embodiment of a wrapped sanitary product such as a tampon in a second stored configuration FIG. 7D is a representation of an embodiment of a wrapped sanitary product such as a tampon in a stored configuration FIG. 10A is a representation of an embodiment of a wrapped sanitary product such as a tampon in a first stored configuration FIG. 10B is a representation of an embodiment of a wrapped sanitary product such as a tampon in an accessible configuration FIG. 10C is a representation of an embodiment of a wrapped sanitary product such as a tampon in an accessible configuration

DETAILED DESCRIPTION OF THE INVENTION

Figure 5C:
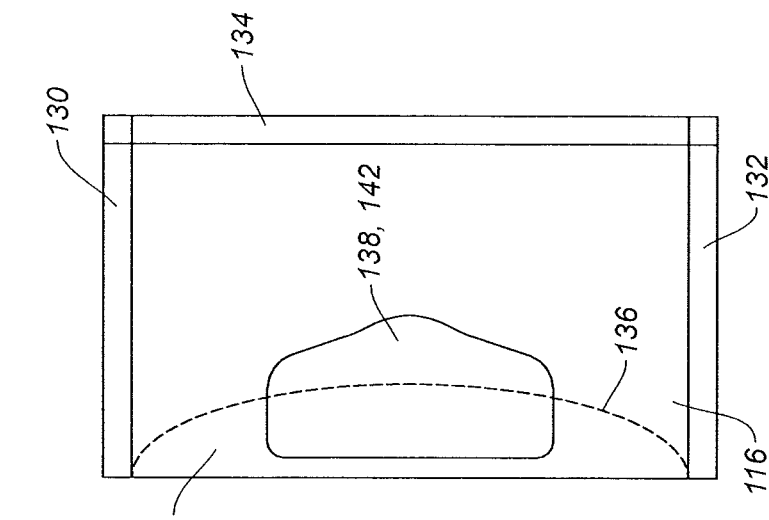
FIG. 5C is a representation of an embodiment of a wrapper
Figure 5B:
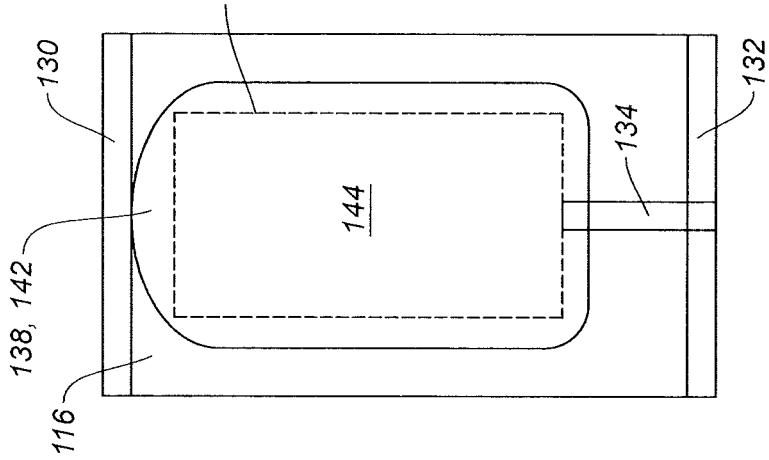
FIG. 5B is a representation of an embodiment of a wrapper
Figure 5A:
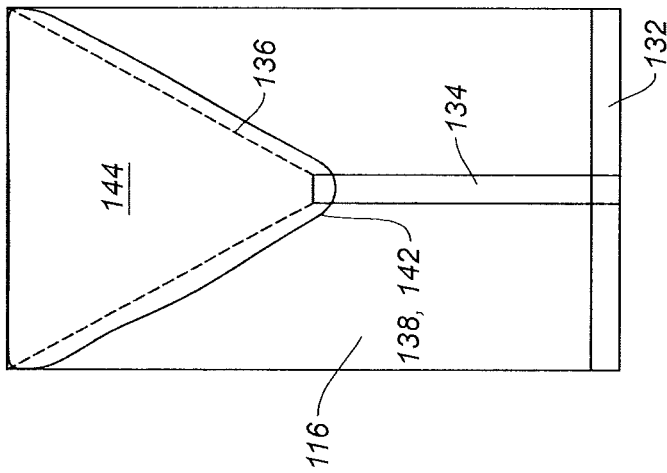
FIG. 5A is a representation of an embodiment of a wrapper

The present disclosure will be discussed hereinafter in detail in terms of the preferred embodiments according to the present disclosure with reference to the accompanying drawings. In the following description, numerous, specific details are set forth in order to provide a thorough understanding of the present disclosure. It will be obvious, however, to those skilled in the art that the present disclosure can be practiced without these specific details. In other instances, well-known structures are not shown in detail in order to avoid unnecessary obscurity of the present disclosure.

As used herein, the term "sanitary products" refers to products that are used for personal hygiene such as, gauze, swabs, cotton pads, tampons, pads, liners, incontinence devices, interlabial pads, pessaries, suppositories and sanitary napkins.

As used herein, the term "soiled sanitary products" refers to any of the aforementioned "sanitary products" in a soiled state. For clarity, the aforementioned sanitary products can be utilized in conjunction or packaged with a delivery device such as a tampon applicator; these delivery devices are also "soiled sanitary products" for the purposes of the present disclosure. For further clarity, other items that come into contact with bodily fluids or bodily areas that the aforementioned products are used in conjunction with can also be considered "soiled sanitary products". For the avoidance of doubt, "soiled sanitary products" are similarly sized to "sanitary products" and thus are able to fit within the wrapper of the present disclosure.

As used herein, the term "tampon" refers to any type of absorbent structure such as, i.e., an absorbent mass that can be inserted into the vaginal canal or other body cavity for the purpose of, such as, i.e., absorbing fluid, aiding in wound healing, and/or for delivering materials such as moisture or active materials such as medicaments. The term "tampon" can also include the combination of an absorbent structure such as, i.e., a tampon pledget, and any type of applicator such as, i.e., a tampon applicator that can be associated with the absorbent structure to facilitate insertion of a tampon into the vaginal canal or other body cavities. A tampon can include known tampon configurations such as, i.e., digital tampons, tampons with traditional plunger type applicators, and/or tampons with compact applicators, or any other tampon.

As used herein, the term "discreet" refers to a wrapper for a sanitary product that does not generate excessive noise, sound or anything else that might be abrasive to the senses. The term "discreet" further refers to the disposal of a soiled sanitary product such that the soiled sanitary product is contained within a wrapper and is thereby likely to retain any mess or unpleasant odor(s) that can be associated with or are resultant of a soiled sanitary product or the unpleasant visual of the soiled sanitary product, or any combination thereof. Further still, the term "discreet" refers to a user's ability to interact with a wrapped sanitary product in a subtle or inconspicuous manner, such that the user can interact with the wrapped sanitary product with ease, comfort and confidence, and furthermore without generating excessive noise, sound or anything else that can be considered abrasive to the senses.

As generally demonstrated in the embodiments of FIGS. 1-5C, the present disclosure relates to wrappers 102 for sanitary products 104 as defined above. The wrapper 102 of the present disclosure includes a port 144 suitably sized to permit grasping of the sanitary product 104 and removal of the sanitary product 104 from within the interior space 120 of the wrapper 102. The wrapper 102 of the present disclosure further provides the port 144 to be sized, shaped and positioned suitably to permit insertion of a soiled sanitary product 114 into the wrapper 102. The wrapper 102 of the present disclosure provides a storage configuration 164 in which the sanitary product 104 is contained within the interior space 120 of the wrapper 102 such that the sanitary product 104 is maintained in a hygienic state. The wrapper 102 of the present disclosure also provides for an accessible or open configuration 166, wherein the sanitary product 104 can be retrieved through a port 144 and removed from the interior space 120 of the wrapper 102. For purposes of the present disclosure, the terms "accessible" and "open" are synonymous. After removal of the sanitary product 104, the wrapper 102 can thereafter accommodate storage of a soiled sanitary product 114. The wrapper 102 can be configured such that it is reclosable, thus providing a second storage configuration 168 for the soiled sanitary product 114, which can thereafter be disposed of. The terms "reclosable" and "resealable" as used herein are the same for the purposes of the present disclosure.

As generally demonstrated in FIG. 1, the wrapper 102 of the present disclosure is a film or sheet of material that has an exterior face 116 and an interior face 118. As used herein, the terms "sheet" and "film" are interchangeable terms, for purposes of the present disclosure. The wrapper 102 has a first end 122 disposed opposite to a second end 124 and a first side 126 disposed opposite to a second side 128. An interior space 120 is defined by the interior face 118 upon the joining of the first side 126 to the second side 128 thereby forming a longitudinal seal 134. The interior space 120 can be further defined by a first end seal 130, a second end seal 132, or both. The first end seal 130 can be formed by the joining of the interior face 118 of the first end 122 to itself. The second end seal 132 can be similarly formed by the joining of the interior face 118 of the second end 124 to itself. It is understood by one skilled in the art that the interior space 120 could be defined by a partial first end seal 130, a partial second end 132 seal, or a partial longitudinal seal 134, or furthermore, the absence of a seal to any of the first end 122, second end 124 or sides 126,128, or combinations thereof. The wrapper 102 could, in the alternative, be completely sealed, have a continuous perimeter seal or variations similar thereto. The wrapper 102 could, in the alternative, be two separate sheets that are at least partially sealed together to form an interior space 120 for storing a sanitary product 104. One of skill in the art understands the seals can be any shape, size, or pattern, and can vary depending on, for instance, i.e., materials used, sealing processes used, and the size of the wrapper 102, amongst other things.

As generally demonstrated in FIGS. 2A-2D, the sanitary product 104 has an insertion end 146 and a withdrawal end 148. A tampon pledget 108 has an insertion end 146 and a withdrawal end 148, and similarly, a tampon applicator 110 has a barrel region 150 and a fingergrip region 152 wherein the fingergrip region 152 is near a withdrawal end 148. Similarly, a plunger 112 has an insertion end 146 and gripping end 146, wherein the gripping end 156 is a withdrawal end 148. In some embodiments, the tampon applicator 110 and plunger 112 are separate, unitary pieces. In other embodiments, the tampon applicator 110 and plunger 112 can be integral with each other or mechanically attached. The plunger 112 telescopically engages the tampon applicator 110 such that the plunger 112 has a range of movement that is encompasses positions where the plunger 112 is at least partially internal to the tampon applicator 110 and positions where the plunger 112 is at least partially external to the tampon applicator 110.

The tampon 106 can further comprise a withdrawal string 158. In applicator systems, a tampon pledget 108 is situated within the barrel region 150 of the tampon applicator 110. The barrel region 150 has a first-most insertion end 146 that typically comprises flexible petals 154 that are rigid enough to maintain the tampon pledget 108 within the barrel region 150 until a sufficient ejection force is provided via the plunger 112; at which point the petals 154 are also flexible enough to deflect upon ejection of the tampon pledget 108 via the sufficient force transmitted by the plunger 112 from within the barrel region 150. In other words, the tampon pledget 108 stays within the barrel region 150 until the user applies a sufficient force to the plunger 112 when the plunger 112 is at least partially telescopically oriented within the tampon applicator 110, such that the insertion end 146 of the plunger 112 applies a sufficient force to the withdrawal end 148 of the tampon pledget 108 thereby forcing the petals 154 of the barrel region 150 open and allowing the tampon pledget 108 to be ejected.

As generally demonstrated in FIGS. 3A-5C, the wrapper 102 comprises a port 144 that allows access to the interior space 120. In other words, the port 144 provides a communication between the exterior of the wrapper 102 and the interior space 120. The port 144 can be oriented in a number of places along the exterior face 116 (and thus also the interior face 118) of the wrapper 102. The port 144 can be any number of geometric shapes and sizes such that the sanitary product 104 can be grasped through the port 144 and removed from the interior space 120. In one embodiment, the port 144 is sized, shaped and positioned such that the withdrawal end 148, gripping end 156, and/or fingergrip region 152 can be discreetly and easily obtained and removed from the wrapper 102. In another embodiment, the port 144 is sized, shaped and positioned such that a soiled sanitary product 114 can be inserted into the interior space 120 of the wrapper 102 via the port 144 such that the wrapper 102 and soiled sanitary product 114 contained therein can be discreetly disposed of. One skilled in the art understands the port 144 of the present disclosure can be combinations of the foregoing embodiments.

The port 144 can be any suitable shape and size. The port 144, for example, can have arcuate and linear portions, can be circular, an ellipsoid, triangular, a rhomboid, a square, rectangular, trapezoidal, a pentagon, hexagon, octagon, decagon, a regular, an irregular, a symmetric, an asymmetric, or any other suitable shape or combinations thereof that meets the aforementioned characteristics.

In some embodiments, a port 144 is configured such that a withdrawal end 148, fingergrip region 152, gripping end 156 and/or plunger 112 are available for discreet grasping by a user. In these embodiments, the port 144 can be sized and shaped to keep a portion of the sanitary product, such as the insertion end 146 and/or barrel region 150, substantially enclosed within the interior space 120 such that it is maintained in a hygienic state until the sanitary product 104 is completely removed from the interior space 120 of the wrapper 102. In another embodiment, the port 144 is configured such that a soiled sanitary product 114 can be discreetly placed within a vacated wrapper 120. In another embodiment, a port 144 is configured in size, shape and position such that it accommodates discreet removal of a sanitary product 104 and the discreet placement of a soiled sanitary product 114 thereafter into the interior space 120 of the wrapper 102. The port 144 can generally have a length dimension 160 that is about 0.20 inches (0.50 cm) to about 6.5 inches (16.51 cm), preferably about 1.00 inches (2.54 cm) to about 5.9 inches (14.99 cm), and most preferably about 1.00 inches (2.54 cm) to about 3.00 inches (7.62 cm). The port can generally have a width dimension 162 that is about 0.30 inches (0.76 cm) to about 1.5 inches (3.81 cm), preferably about 0.30 inches (0.76 cm) to about 1.25 inches (3.18 cm.

In one embodiment, the port 144 is positioned at least partially over a first end 122 of the wrapper. In one embodiment, the port is positioned at least partially over a second end 124 of the wrapper (not shown). In one embodiment, the port 144 is positioned such that it is partially adjacent to a longitudinal seal 134. In another embodiment, the port 144 can be positioned such that it is at least partially over a first end 122 of the wrapper 102 and is adjacent to a longitudinal seal 134. In another embodiment, the port 144 can be positioned such that it is at least partially over a second end 124 of the wrapper 102 and is adjacent to a longitudinal seal 134 (not shown). In another embodiment, the port 144 can be positioned such that it is adjacent to a longitudinal seal 134. In another embodiment, the port 144 can be positioned such that it is at least partially over a first end 122 of the wrapper 102 and partially over longitudinal seal 134. In one embodiment, the port 144 is positioned such that is partially over longitudinal seal 134.

The wrapper 102 has a flap 136 that seals the wrapper 102 in a storage configuration 164. In a storage configuration 164, the flap 136 is positioned over the port 144 and provides a sealed wrapper 102. In one embodiment, the flap 136 is integral with the wrapper 102. The wrapper 102 can undergo a process 172 that cuts, slits, perforates, or creates a line of weakness thereby providing at least a partial perimeter of the flap 136. The flap 136 can comprise a tab 140 that permits easier removal of the flap 136 from the wrapper 102 thereby revealing at least part of the port 144. The tab 140,142 can be oriented in any number of positions, and the tab 140,142 can be any shape or size such that the tab facilitates the process of opening, removing the sanitary product 104, replacing a soiled sanitary product 114, and/or closing/ resealing the wrapper for disposal. In some embodiments, there can be one or more tabs 140,142.

In one embodiment, the flap 136 at least partially covers the port 144. In other embodiments, the flap 136 can be a separate component or material from the wrapper 102. The flap 136 can further comprise a sticker 138. The sticker 138 at least partially covers the port 144. In embodiments having both a flap 136 and a sticker 138, the flap 126 and sticker 138 provide complete coverage of the port 144. The sticker 138 is at least partially sealable to the exterior face 116 such that the wrapper 102 has a storage configuration 164 that maintains the sanitary environment of the interior space 120 and the sanitary product 102 contained therein. In one embodiment, the sticker 138 is at least partially sealable to the flap 136. The sticker 138 can be at least partially removed from the exterior face 116 of the wrapper 102 such that at least a portion of the port 144 is exposed. The sticker 138 can be at least partially removed from the exterior face 116 such that the sticker also at least partially removes the flap 136 thereby exposing at least a portion of the port 144. The sticker 138 can further comprise a tab 142 that permits easier removal of the sticker 138, the flap 136, or both from the exterior face 116. The tab 142 of the sticker 138 can have a tacky material such that it is at least partially sealable to the exterior face 116.

In any event, the flap, 136, the sticker 138, the tab 140,142 and any combinations thereof, are positioned, sized and shaped to facilitate the process of opening, removing the sanitary product 104, replacing a soiled sanitary product 114, and/or closing/resealing the wrapper for disposal.

The flap, 136, the sticker 138, the tab 140,142 and any combinations thereof, can be any suitable shape and size. The flap, 136, the sticker 138, the tab 140,142 and any combinations thereof, for example, can have arcuate and linear portions, can be circular, an ellipsoid, triangular, a rhomboid, a square, rectangular, trapezoidal, a pentagon, hexagon, octagon, decagon, a regular, an irregular, a symmetric, an asymmetric, or any other suitable shape or combinations thereof that meets the aforementioned characteristics.

In one embodiment as exemplified in at least FIGS. 9A-9D, the flap, 136, the sticker 138, the tab 140,142 and any combinations thereof, opens at an angle across the length of the wrapper such that the surface area of the port 144 can be larger than if the flap, 136, the sticker 138, the tab 140,142 and any combinations thereof, opened along the length or width of the wrapper. This embodiment also allows for the flap, 136, the sticker 138, the tab 140,142 and any combinations thereof, to have a greater surface area and thus be able to protect/shield a greater surface area from spillage of/related to the soiled sanitary product 114 as the user places the soiled sanitary product 114 into the wrapper 102. In other embodiments, the flap, 136, the sticker 138, the tab 140,142 and any combinations thereof, can reveal a smaller port 144 such that the integrity of the sanitary product 104 is maintained until the user withdraws the product from the wrapper 102. In yet further embodiments, the flap, 136, the sticker 138, the tab 140,142 and any combinations thereof, can be smaller such that it requires less movement of the flap between open and closed positions. One skilled in the art understands that the present disclosure provides for embodiments where the flap, 136, the sticker 138, the tab 140,142 and any combinations thereof, can be large or small and the port 144 can be large or small, combinations thereof, so long as a user is able to open, remove a sanitary product 104, place a soiled sanitary product 114 in the vacated wrapper 102, and close the wrapper 102.

The flap 136 can be positioned such that it accommodates removal of the flap 136 by the user's dragging the flap 136 downward from a position closer to the first end 122 of the wrapper 102 to a position closer to the second end 124 of the wrapper 102. This embodiment can be advantageous in that it allows a user, in an accessible configuration 166, to pin the flap 136 and hold the wrapper 102 with one hand while holding either the sanitary product 104 or the soiled sanitary product 114 in the other hand. In the alternative, the flap 136 can be positioned such that it accommodates removal of the flap 136 by the user's pulling the flap 136 upward from a position closer to the second end 124 of the wrapper to a position closer to the first end 122 of the wrapper 102. This embodiment can be advantageous as potentially allows the opportunity for the user to have more leverage in removing the flap 136. In another embodiment, the flap 136 can be positioned such that it accommodates removal of the flap 136 in a lateral direction. In this embodiment, the flap 136 can be flipped over the first end 122 of the wrapper 102 and be held against the backside of the wrapper 102 (i.e. the face of the wrapper 102 that does not have the port 144). In other embodiments, the flap 136 can be positioned such that it accommodates removal of the flap 136 in any combination of upward, downward and lateral. In embodiments where the flap 136 further comprises a sticker 138, the flap 136 or sticker 138 or both can be positioned to accommodate removal of the flap 136 or sticker 138 or both in an upward, downward or lateral direction, or any combination thereof. In embodiments wherein a flap 136 further comprises a tab 140, the tab 140 assists in the user in moving the flap 136 in an upward, downward or lateral direction, or any combination thereof. In embodiments wherein a sticker 138 further comprises a tab 142, the tab 142 assists the user in moving the flap 136 in an upward, downward, or lateral direction, or combinations thereof. One skilled in the art understands that the flap 136, sticker 138, tab 140,142 and any combinations thereof can be moved in a direction that allows for either discreet removal of the sanitary product 104 from the interior space 120 of the wrapper 102 through the port 144 or discreet placement of a soiled sanitary product 114 into the vacated wrapper 102, or both. In any of the aforementioned embodiments, port 144, the flap 136, sticker 138, tab 140,142, and any combinations thereof permit going from a storage configuration 164 to an accessible configuration 166 in a discreet manner or from an accessible configuration 166 to a second storage configuration 168 in a discreet manner, or both. In other words, the port 144, the flap 136, the sticker 138, the tab 140,142 and any combinations thereof are sized, shaped and positioned to provide a wrapper 102 for a sanitary product 104 and/or a wrapped sanitary product 100 that can be stored, used and interacted with in a discreet manner.

The flap 136 and sticker 138 can be any suitable shape and size. The flap 136 or sticker 138 or both, for example, can have arcuate and linear portions, can be circular, an ellipsoid, triangular, a rhomboid, a square, rectangular, trapezoidal, a pentagon, hexagon, octagon, decagon, a regular, an irregular, a symmetric, an asymmetric, or any other suitable shape or combinations thereof that meets the aforementioned characteristics.

In embodiments where the flap 136 is integral with the wrapper 102, the flap 136 may be scored, have slits, score lines, cuts or other lines of weakness, about the integral portion 145 where the flap 136 and wrapper 102 meet and form a boundary of the port 144. The scored integral portion 145 assists in the wrapper 102, once opened, to remain in an open position 166 (i.e., folded downward, upward, over the top of a first end 122 or a second end 124, to a side, over the side, etc.). This is advantageous in that the score creates an enhanced hinge about which the flap 136 can bend and remain in an open position 166. In embodiments comprising a sticker 138, the sticker 138 may be located such that an end coincides with the integral and/or scored portion 145 of the flap 136 or is located such that the sticker 138 does not overlap the integral portion 145 of the flap 136 and wrapper 102, and thereby enables the flap 102 to remain in an open position 166. In some embodiments, the flap 136 may have an additional layer and/or have a sticker 138 such that the weight of the flap 136 and/or sticker 138 is sufficient to bias the flap 136 and/or sticker 138 in an open position 166 once the flap 136 and/or sticker 138 has been grasped and pulled from/separated from the wrapper 102. In embodiments also having a tab 140,142, the same principles previously discussed for the flap 136 and sticker 138 also apply.

In other embodiments, the flap 136, sticker 138, tab 140,142, or combinations thereof, may be oriented such that the center of mass the flap 136, sticker 138, tab 140,142, or combinations thereof, is positioned beyond the midsection 147 of the flap 136, sticker 138, tab 140,142, or combinations thereof. In these embodiments, the center of mass is located towards the end portion 149 of the flap 136, sticker 138, tab 140,142, or combinations thereof, which is initially grasped by the user such that the wrapper 102, once opened, will remain in an open position 166. The center of mass in its location between the midsection 147 of the flap 136, sticker 138, tab 140,142, or combinations thereof, and the opening end of the flap 136, sticker 138, tab 140,142, or combinations thereof, biases the flap 136, sticker 138, tab 140,142, or combinations thereof, to remain in an open configuration 166. In any event, it is preferable to have a flap that can be biased in an open position 166 after the flap 136, sticker 138, tab 140,142, or combinations thereof, has been grasped by the user in preparation for removing the sanitary product 104.

In other embodiments, the flap 136, sticker 138, tab 140,142, or combinations thereof, are of a material that is sufficiently rigid or stiff such that a user is able to flick the flap 136, sticker 138, tab 140,142, or combinations thereof, from an open position 166 to a second storage configuration 168. This is advantageous in that it requires less manipulation in order to reseal the wrapper 102 and discreetly dispose of the soiled sanitary product 114.

The wrapper 102 has an accessible configuration 166 wherein the flap 136 is at least partially opened revealing the port 144 and the sanitary product 104 therein. In embodiments having a sticker 138, the sticker 138 is at least partially removed thereby revealing at least part of the port 144 and thus the sanitary product 104 contained within the interior space 120. The sanitary product 104 is then removable from the interior space 120 via the port 144. Once the interior space 120 is vacated, the user is able to insert a soiled sanitary product 114 into the interior space 120.

The wrapper 102 has a second storage configuration 168 wherein the flap 136 is able to at least partially reseal to the wrapper 102 in order to contain the soiled sanitary product 114 for disposal. In one embodiment, the sticker 138 is able to at least partially reseal to the exterior face 116 thereby at least partially covering the port 144 and containing the soiled sanitary product 114 in the interior space 120, in preparation for disposal. In one embodiment, the flap 136, sticker 138, or both completely cover the port 144 and reseal the wrapper 102 thereby containing the interior space 120 containing the soiled sanitary product 114, in preparation of disposal. Preferably, the wrapper 102 is able to provide all three configurations in a discreet manner. In other words, the wrapper 102 should be sealable and resealable in a quiet or softer manner.

The sticker 138 comprises a tacky or adhesive material that permits the sticker to provide for an initial storage configuration 164 in a sealed state and a second storage configuration 168 in a resealed state. For example, the sticker 138 can comprise, i.e., polypropylene, polyesters, acetate, vinyl, polyethylene terephthalate, foil, wax, resin, paper, nonwoven, or any other suitable material or combinations thereof. The sticker 138 material can be any suitable thickness, such as, i.e., in a range of about 0.01 mil to 20 mils, and preferably, in a range of about 1.0 to 19.0 mils. One of skill in the art understands that it is well within the bounds of the present disclosure to have a sticker with any thickness and furthermore to have a sticker with any number of layers. In 138 one embodiment, the sticker 138 has a suitable peel force such that it can be in a stored configuration 164 where the sticker 128 is sealed to the wrapper 102, an accessible configuration 166 where the sticker 138 is not sealed to the wrapper 102, and a second storage configuration 168 wherein the sticker 138 can be resealed to the wrapper 102.

The wrapper 102 can be formed from any suitable material, such as, i.e., a polymeric film, such as, for example, polyolefin, such as, i.e., polyethylene, polypropylene, polyesters such as, i.e., synthetic polyesters, polyamides, polyvinyl chlorides, ethylene-vinyl acetate copolymers, and/or other suitable films, a nonwoven, a formed film, a paper, or a fabric comprises of suitable material such as polyethylene, polypropylene, polyester, cellulose, rayon, cotton, super absorbent material such as polyacrylate or combinations thereof. In one embodiment, the wrapper 102 material is comprised of a water-impermeable material such as, for example, a co-extruded laminate that comprises a polyolefin layer and a layer of a vinyl acetate material. In one embodiment, the co-extruded laminate includes a layer of polyethylene (PE) base and a layer of ethylene vinyl acetate (EVA) sealant. Alternatively, a layer of polyester such as, for example, polyethylene terephthalate (PET) or polypropylene (PP) can be used in place of the PE layer. In another embodiment, the wrapper 102 material comprises voids within any of the layer(s) or interfaces between the layers.

The wrapper 102 material can be a sheet or film of material that forms a barrier to prevent air, moisture and contaminates from entering the internal chamber and contacting the sanitary product 104 enclosed therein. In one embodiment, the material is a thermoplastic material and is comprised of a single sheet of synthetic polymeric material and, optionally, a laminate comprising two or more layers of thermoplastic materials.

In one embodiment, the wrapper 102 can include a first liquid impermeable material and a second absorbent material. For example, the first liquid impermeable material can be utilized for the exterior face 116 of the wrapper 102 such that contaminants and moisture are kept from the sanitary product 104. In another embodiment, an absorbent material can be utilized for the interior face 118 of the wrapper 102 such that fluid from a soiled sanitary product 114 would be absorbed by the interior face 118. Alternatively, the wrapper 102 can have a first liquid impermeable material utilized for the exterior face 116 and the same or a different liquid impermeable material for the interior face 116.

In another embodiment, the wrapper 102 can include a material providing an improved user sensory experience. For instance, the wrapper 102 can include a material that assists in providing a discreet storage and use process for the user. In one embodiment, the wrapper 102 can include a material that has a soft, smooth or otherwise appealing texture. In another embodiment, the wrapper can include a material that makes very little sound upon disturbing or jostling the wrapper. For instance, wrapper 102 made of PE material has been found to produce less noise during opening than a wrapper that is comprised of PET or PP. In one embodiment, a wrapper is comprised of PET or PP.

In another embodiment, the wrapper 102 can include a fragrance or comprise odor-neutralizing agents. In another embodiment, the wrapper 102 can include a material that is otherwise visually pleasing (i.e. glossy or having printing, colors or graphics). One skilled in the art understands that the wrapper 102 of the present disclosure can comprise one or more layers of materials that provide any or all of the benefits so described within the present disclosure.

In one embodiment, a thickness of the wrapper 102 material is in a range of about 0.01 mil to 9.00 mils, and preferably, in a range of about 1.0 to 7.0 mils. One of skill in the art understands that it is well within the bounds of the present disclosure to have a wrapper 102 with any thickness and furthermore to have a wrapper with any number of layers.

In one embodiment, the wrapper 102 material is a multiple layer film that can be joined in any suitable manner for forming multiple layer packaging, such as, i.e., ultrasonic bonding, thermal bonding, mechanical bonding, adhesive bonding, extrusion lamination, and other methods. In one embodiment, the wrapper 102 material is heat sensitive such that the perimeter seal is formed by, for example, a heat press, sonic welding, continuous bead hot melt adhesive, or any other suitable means for joining the first side to the second side of the wrapper 102. In one embodiment, the wrapper 102 material is comprised of a coextruded laminate that includes layers of polypropylene (PP) and EVA, with the EVA layer disposed inside the PP layer of the wrapper 102. The co-extruded laminate of PP/EVA is available from Pliant Corporation (Newport News, Va.) as product code XP9475A. In embodiments where a multiple layer film comprises the wrapper 102, the film can be manufactured prior to assembling a sanitary product 104 into a wrapper 102. In some embodiments, the film can be formed in-line with the process of wrapping the sanitary product 104. In other embodiments, the film can be formed in a separate location.

Figure 6:
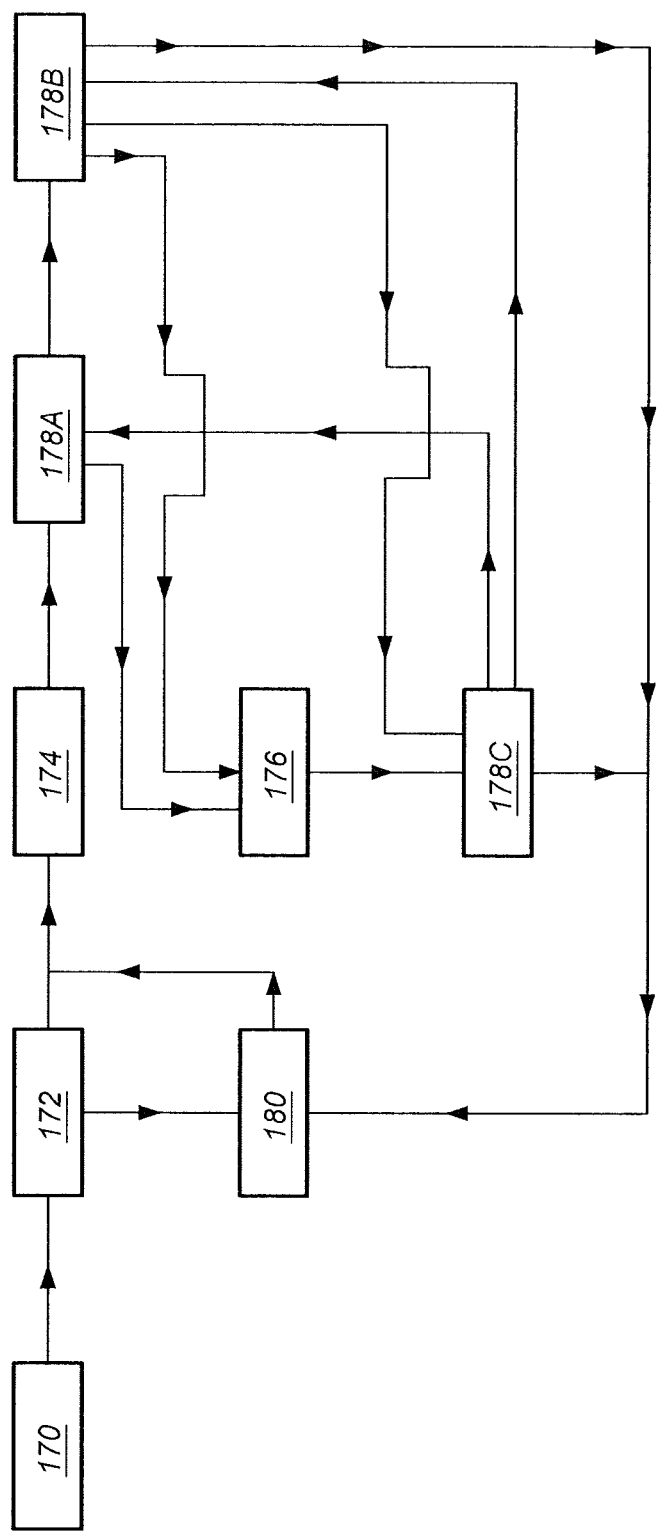
FIG. 6 is a representation of an embodiment of a method of wrapping a sanitary product
Figures 8A, 8B:
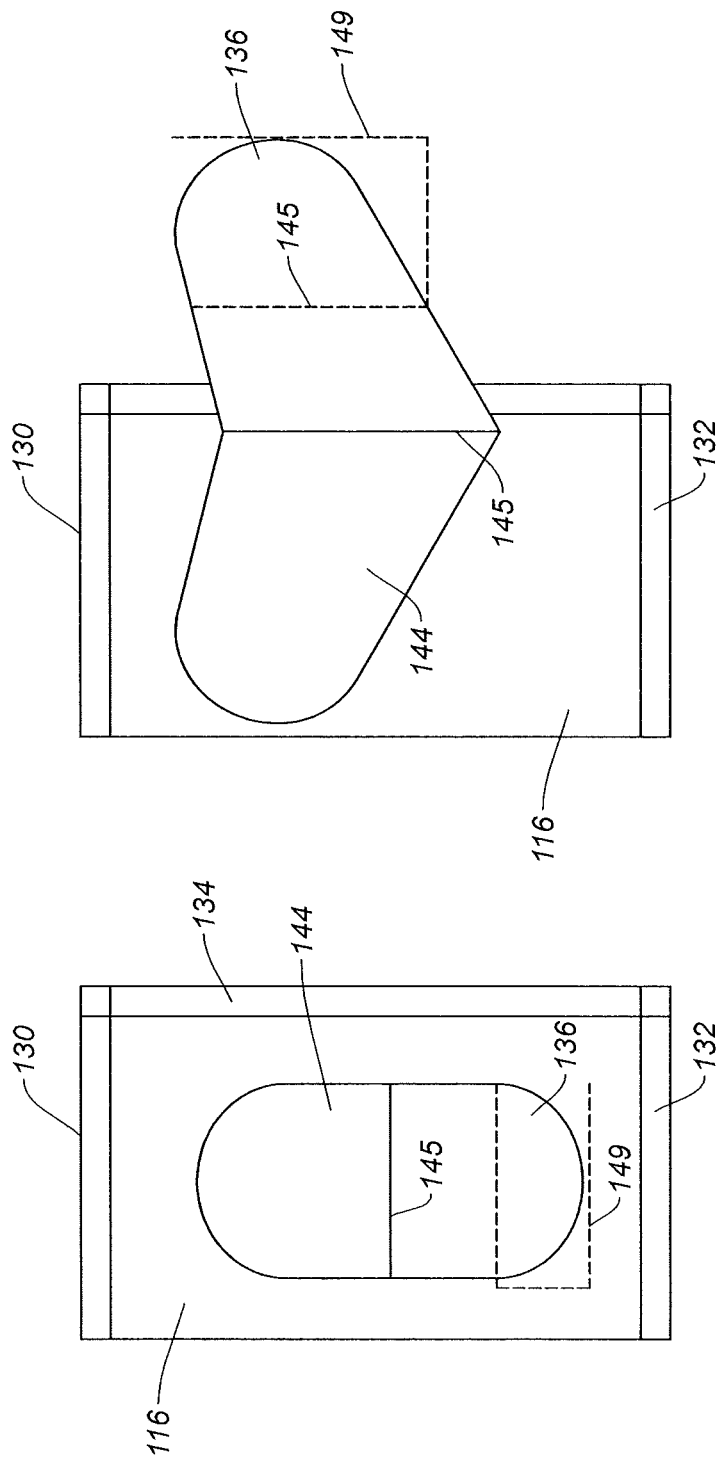
FIG. 8A is a representation of an embodiment of a wrapped sanitary product such as a tampon in an accessible configuration
FIG. 8B is a representation of an embodiment of a wrapped sanitary product such as a tampon in an accessible configuration
Figures 9A, 9B, 9C, 9D:
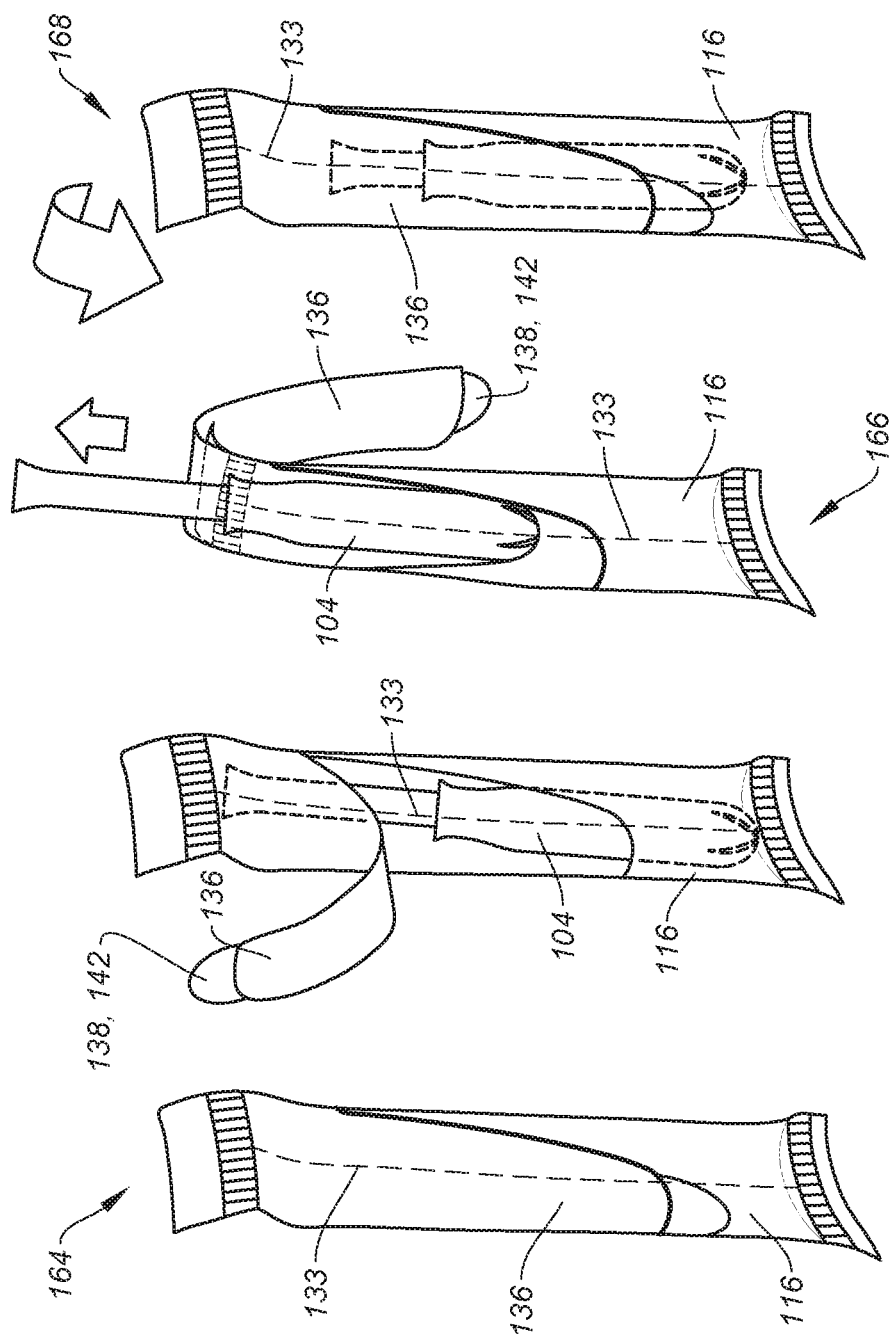
FIG. 9A is a representation of an embodiment of a wrapped sanitary product such as a tampon in a first stored configuration
FIG. 9B is a representation of an embodiment of a wrapped sanitary product such as a tampon in an accessible configuration
FIG. 9C is a representation of an embodiment of a wrapped sanitary product such as a tampon in an accessible configuration
FIG. 9D is a representation of an embodiment of a wrapped sanitary product such as a tampon in a second stored configuration

An exemplary embodiment of a method of wrapping the sanitary product 104 according to the present disclosure is described with reference to FIG. 6. Again, for ease of discussion, the method of wrapping the sanitary product 104 is discussed herein by way of example in use with a tampon 106 embodiment. Of course, it is contemplated by the present disclosure for method to find use with any other sanitary product 104.

Method includes a first step 170 in which film is cut into a desired dimension for packaging sanitary products. In some embodiments, for example, the step 172 of making a cut, die cut, laser cut, a line of weakness, scoring, laser scoring, slitting, punching or perforation for a port 144 or flap 136 or both can be done simultaneously with the first step 170 or sequentially to the cutting along cut line. In other embodiments, for example, step 172 of making a cut, die cut, laser cut, a line of weakness, scoring, laser scoring, slitting, punching or perforation step can be done in a separate step. The step 172 for making, for example, a cut, die cut, laser cut, a line of weakness, scoring, laser scoring, slitting, punching or perforation step will be done such that it at least partially coincides with the perimeter of the port 144, or the perimeter of the flap 136, or both. In one embodiment, an integral flap 136 is formed. In another embodiment, the flap 136 is capable of being completely removed from the wrapper 102. In yet another embodiment, wrapper 102 material is completely removed such that a port 144 remains (not shown). In some embodiments, the flap 136 or perimeter of a port 144, or both is formed in the film by step 172 to be sized, shaped and positioned such that the flap 136 or perimeter of a port 144, or both provides for discreet removal of a sanitary product 104 from within a wrapper 102, for discreetly reclosing said wrapper 102, or both.

The method further includes another step 174 in which the film is rolled over to form a tube-like shape. In other sanitary product 104 embodiments, this tube-like shape can be another shape that more accurately reflects the shape of the sanitary product 104, such as, i.e., a prismatic shape. This step can be followed by another step 178A in which an at least partial longitudinal seal 134 is formed by at least partially joining a first side 126 to a second side 128, thereby forming the film in a tube-like shape.

The method can further comprise another step 176 in which a sanitary product 104, such as a tampon 106, is inserted into the tube-like shape of the wrapper 102. In some embodiments, the tampon 106 is inserted into the wrapper so that the withdrawal end 148 of the tampon 106 is proximate to the port 144 and the insertion end 146 of the tampon 106 is remote from the port 144. In some embodiments, the fingergrip region 152 of the tampon applicator 110, the gripping end 156 of the plunger 112, or both can be proximate to the port 144 such that the petals 154 of the barrel region 150 or the insertion end 146 of the plunger 112, or both can be remote to the port 144. Of course, it is contemplated by the present disclosure for tampon 106 or any sanitary product 104 to be inserted into the wrapper 102 in any desired orientation.

In one embodiment step 178A can be followed by step 176 as described above. Step 176 can also be followed by steps 178B or 178C, or both in the step 178C in which a first end seal 130 is at least partially formed and the step 178B in which the second end seal 132 is at least partially formed. First end seal 130 is formed by joining the interior face 118 of first end 122 onto itself. Likewise, second end seal 132 is formed by joining the interior face 118 of the second end 124 onto itself. In some embodiments, either the first end 122 or second end 124 or both are only partially joined such that there are only a partial first end seal 130, second end seal 132 or both. In other embodiments, the first end 130 or the second end 132 cannot be joined such that there is no first end seal 130 or no second end seal 132, or no end seals at all. One of skill in the art understands that step 178A can be followed by step 176, 178B or 178C in any order.

In other sanitary product 104 embodiments, the sanitary product 104, may be placed on an interior face 118 of the wrapper 102 prior to forming a first end seal 130, a second end seal 132, and/or a longitudinal seal 134. Depending on the sanitary product 104, the longitudinal seal 134 could be oriented such that it appears as a horizontal seal 133.

In other embodiments, the step 172 of making a cut, die cut, laser cut, a line of weakness, scoring, laser scoring, slitting, punching or perforation is done to at least partially coincide with the perimeter of the port 144 or flap 136 or both, where the port 144 or flap 136 or both at least partially coincide(s) with or is adjacent to a first end 122, a first end seal 130, a second end 124, a second end seal 132, a first side 126 or a second side 128, a longitudinal seal 134 or any combinations thereof. In these embodiments, the portion(s) of the at least partial first end seal 130, or at least partial second end seal 132, or at least partial longitudinal seal 134, or any combinations thereof, which are not joined, can coincide with the perimeter of the port 144 or flap 136 or both. In other embodiments where the first end 122 or second end 124 is not joined, a portion of the perimeter of the port 144 or flap 136 or both can coincide with that first end 122 or second end 124.

The method can further comprise the step 180 of applying a sticker 138 to the film. The sticker 138 can at least partially coincide with the port 144, the perimeter of the port 144, the flap 136 or the perimeter of the flap 136 and the area of the exterior face 116 surrounding the port 144 or flap 136 or both. The sticker 138 can be applied sequentially after, for example, the step 172 of making a cut, die cut, laser cut, a line of weakness, scoring, laser scoring, slitting, punching or perforation is completed, or after steps 174, 176, 178A, 178B and 178C have been completed.

An exemplary embodiment for a method of storing and utilizing a wrapped sanitary product 100 and soiled sanitary product 114 of the present disclosure is also provided. The method involves the steps of storing a wrapped sanitary product 100 such that the wrapped sanitary product 100 is maintained in a storage configuration 164; removing a flap 136 from a sealed wrapper 102 to reveal a port 144 that provides access to an interior space 120 within said wrapper 102 such that the wrapped sanitary product 100 is in an accessible configuration 166; removing a sanitary product 104 from a wrapper 102 through the port 144 thereby vacating said interior space 120 of the wrapper 102; placing a soiled sanitary product 114 through the port 144 into the interior space 120 of the wrapper 102; replacing the flap 136 such that the flap 136 reseals the wrapper 102 and permits discreet disposal of the soiled sanitary product 114 within the wrapper 102. In some embodiments, the flap 136 further comprises a tab 140 that can be utilized to assist in the step of removing the flap 136 from the sealed wrapper 102 and also assists in the step of resealing the flap 136 to the wrapper 102 such that the soiled sanitary product 114 is resealed in the wrapper 102 in a second storage configuration 168. In some embodiments, the flap 136 further comprises a sticker 138. In some embodiments, the sticker 138 further comprises a tab 142 that assists in the step of removing the flap 136 from the sealed wrapper 102 such that the wrapped sanitary product 100 is in an accessible configuration 166. In embodiments wherein a flap 136 further comprises a sticker 138, the sticker 138 (and optionally tab 142) assists in the step of resealing the flap 136 to the wrapper 102 such that the soiled sanitary product 114 is resealed into the wrapper 102 in a second storage configuration 168.

An exemplary embodiment for a method of using a sanitary product 104 of the present disclosure is also provided. The method of using a sanitary product 104 comprises the steps of: storing a wrapped sanitary product 100 comprising a wrapper 102, and a sanitary product 104 having an insertion end 146 and a withdrawal end 148; wherein the sanitary product 104 is contained within an interior space 120 of the wrapper 102, wherein the wrapper 102 has a flap 136 that is sealed to the wrapper 102 thereby maintaining the sanitary product 104 in a hygienic condition within the interior space 120 of the wrapper 102; opening the wrapped sanitary product 100 by removing the flap 136 such that the flap 136 is no longer sealed to the wrapper 102, thereby revealing a port 144 in the wrapper 102 that permits access to the sanitary product 104; removing the sanitary product 104 from the wrapper 102 by grasping the withdrawal end 148 of the sanitary product 104 through the port 144 in the wrapper 102; placing a used sanitary product 114 through the port 144 in the wrapper 102; and closing the flap 136 over the port 144 such that the used sanitary product 114 is sealed within the interior space 120 of the wrapper 102. The method can further comprise the step disposing of the wrapper 102 containing the used sanitary product 114. In some embodiments, the flap 136 can further comprise a tab 140, a sticker 138, or a flap 142 that assist in the opening of the wrapper 102 or resealing of the wrapper 102, or both.

Although the present disclosure has been described and illustrated with reference to specific exemplary embodiments thereof, it is not intended that the invention be limited to those exemplary embodiments. Those skilled in the art will recognize that variations and modifications can be made without departing from the true scope of the present disclosure as defined by the claims that follow. For instance, features disclosed in connection with any one embodiment can be used alone or in combination with each feature of the respective other embodiments.

What is claimed is:

1. A wrapped sanitary product, comprising:
a sanitary product; and
a wrapper having an interior face that is disposed opposite to an exterior face, said interior face and said exterior face having a first end that is disposed opposite to a second end and a first side that is disposed opposite to a second side, wherein said wrapper forms an interior space defined by said interior face, the joining of said first side and said second side to form a longitudinal seal, the joining of said first end onto itself to form a first end seal, and the joining of said second end onto itself to form a second end seal, said longitudinal seal being disposed along a middle portion of a width of said wrapper such that said longitudinal seal is inward from and substantially parallel to a first longitudinal edge and a second longitudinal edge;
wherein said wrapper has a port having a first end and a second end, said port located inwardly of said first longitudinal edge and said second longitudinal edge of said wrapper, said first end of said port located proximal to and inward of said first end, said port providing access to said interior space from outside of said wrapper, said port has a width dimension between about 0.30 inches to about 1.25 inches and a length dimension between about 1 inches to about 3 inches such that said port is sized, shaped and positioned to permit discreet removal of said sanitary product from within said wrapper, said wrapper having a flap that is sealable to said wrapper to provide a complete closure around said interior space;
wherein said wrapped sanitary product has a storage configuration such that said sanitary product is contained within said interior space; wherein said flap is in a sealed position such that said interior space is not accessible by said port, which flap is integral to said wrapper;
wherein said wrapper has an accessible configuration such that said sanitary product can be removed from said interior space, wherein said flap is at least partially removed from said port such that said interior space is accessible; and
wherein said wrapper has a second storage configuration such that said sanitary product has been removed from said interior space thereby leaving the interior space vacated, and wherein flap is at least partially resealable to said wrapper thereby resealing said interior space; and a sticker independent of the flap and attached to the flap, which sticker is at least partially detachable from said wrapper in said accessible configuration, and wherein said sticker is sealable to the exterior face to hold the flap in a position wherein the wrapper, including the flap, provide a complete closure around said interior space in said storage configuration and in said second storage configuration;

wherein said flap is pivotally attached to said wrapper at a position between said second end of said port and a portion of said interior space configured to receive at least a portion of said sanitary product, and configured such that said flap can be rotated about said pivotal attachment towards said second end;

wherein said pivotal attachment is positioned such that said flap and said sticker are pivotable towards said second end;

wherein said flap and said sticker attached to the flap have a combined weight that is sufficient to rotate at least a portion of said flap about said pivotal attachment and thereby bias said flap in said accessible configuration;

wherein said sticker has a length dimension and a width dimension that are greater than said length dimension and said width dimension of said port, respectively; and wherein said sticker and said flap, when rotated into a completely open position, do not extend beyond the second end of the wrapper.

2. The wrapped sanitary product of claim 1, wherein said sanitary product is a tampon, comprising:
a tampon pledget having an insertion end and a withdrawal end;
a tampon applicator having a barrel region and a fingergrip region; and
a plunger having an insertion end and a gripping end;
wherein said tampon has a storage configuration wherein said tampon pledget is within said barrel region of said applicator; and
wherein said plunger is telescopically engaged in said tampon applicator such that said insertion end of said plunger at least partially touches said withdrawal end of said tampon pledget such that a user can eject said tampon pledget out of said barrel region of said applicator by gripping said fingergrip region of said applicator and gripping said gripping end of said plunger.

3. The wrapped sanitary product of claim 1, wherein said port is sized, shaped and positioned to permit a soiled sanitary product to be discreetly placed through said port into said wrapper.

4. The wrapper of claim 1, wherein the port extends at an angle across a length of the wrapper between the first side and the second side.

5. The wrapper of claim 4, wherein the port extends beyond a midpoint between the first end and the second end.

6. The wrapped sanitary product of claim 1, wherein said wrapper material comprises polyethylene material that assists in providing discreet storage and use of said wrapped sanitary product.

7. The wrapped sanitary product of claim 6, wherein said wrapper has one or more colors and graphics.

8. The wrapped sanitary product of claim 6, wherein said sheet has a thickness between about 1.0 mils and about 7.0 mils.

9. The wrapped sanitary product of claim 6, wherein said wrapper comprises a second layer of material, wherein second layer comprises polyester, polypropylene, polyethylene, PET, EVA, or combinations thereof.

10. The wrapped sanitary product of claim 1, wherein said wrapper comprises a second layer of material, wherein said second layer comprises polyester, polypropylene, polyethylene, PET, EVA, or combinations thereof.

11. A wrapped sanitary product, comprising:
a sanitary product having an insertion end and a withdrawal end, said sanitary product comprising:
a tampon pledget having an insertion end and a withdrawal end, said withdrawal end having a withdrawal string;
a tampon applicator having a barrel region and a curved fingergrip region having a flared end; and
a plunger having an insertion end and a flared gripping end;
wherein said tampon has a storage configuration wherein said tampon pledget is within said barrel region of said applicator; and
wherein said plunger is telescopically engaged in said tampon applicator such that said insertion end of said plunger at least partially touches said withdrawal end of said tampon pledget such that a user can eject said tampon pledget out of said barrel region of said applicator by gripping said fingergrip region of said applicator and gripping said gripping end of said plunger; and
a wrapper for said sanitary product, said wrapper comprising:
a sheet of material having an interior face that is disposed opposite to an exterior face, said interior and exterior faces having a first end that is disposed opposite to a second end, and a first side that is disposed opposite to a second side, wherein said wrapper forms an interior space suitably sized for said sanitary product to be stored therein and defined by said interior face, a longitudinal heat seal joining said first side and said second side, said longitudinal seal being disposed along a middle portion of a width of said wrapper such that said longitudinal seal is inward from and substantially parallel to a first longitudinal edge and a second longitudinal edge, a first end heat seal joining a first end onto itself and a second end heat seal joining of said second end onto itself, said exterior face having a front face and back face opposite to said front face, said back face including said longitudinal seal;
wherein said wrapper is openable by a perforation, score, punch, line of weakness, or slit disposed parallel to and inward of a first end and a second end on said front face such that upon opening said wrapper, a port is created and positioned such that either a portion of said longitudinal seal is revealed or a portion of said plunger covering said longitudinal seal is revealed;
wherein said plunger or said grip end of said sanitary product is oriented towards perforation, score, punch, line of weakness, or slit; and
wherein said sheet has a thickness between about 0.01 mils and about 9.00 mils;
wherein said wrapper forms a tube-like shape; and
wherein said wrapper comprises polyethylene material that assists in providing discreet storage and use of said wrapped sanitary product.

12. The wrapped sanitary product of claim 11, wherein said wrapper comprises a second layer of material, wherein said second layer of material comprises polyethylene.

13. The wrapped sanitary product of claim 12, wherein said wrapper comprises a third layer of material, wherein said third layer comprises polyester, polypropylene, polyethylene, PET, EVA, or combinations thereof.

14. The wrapped sanitary product of claim 13, wherein said third layer of material comprises polyethylene.

15. The wrapped sanitary product of claim 11, wherein said sheet has a thickness between about 1.0 mils and about 7.0 mils.

\* \* \* \* \*